(12) United States Patent
Rust et al.

(10) Patent No.: US 8,519,956 B2
(45) Date of Patent: Aug. 27, 2013

(54) SYSTEM AND METHOD FOR DICOM COMPLIANT DISPLAY OF ULTRASOUND IMAGES IN VARYING AMBIENT LIGHT

(75) Inventors: David Rust, Seattle, WA (US); Joseph M. Luszcz, Andover, MA (US)

(73) Assignee: Koninklijke Philips N.V., Eindhoven (NL)

( * ) Notice: Subject to any disclaimer, the term of this patent is extended or adjusted under 35 U.S.C. 154(b) by 1271 days.

(21) Appl. No.: 12/307,373

(22) PCT Filed: Jul. 3, 2007

(86) PCT No.: PCT/IB2007/052589
§ 371 (c)(1),
(2), (4) Date: Jan. 5, 2009

(87) PCT Pub. No.: WO2008/007301
PCT Pub. Date: Jan. 17, 2008

(65) Prior Publication Data
US 2009/0203999 A1    Aug. 13, 2009

(51) Int. Cl.
*G06F 3/033*           (2013.01)
(52) U.S. Cl.
USPC ............... 345/158; 345/63; 345/72; 600/453; 600/459
(58) Field of Classification Search
USPC .............. 345/73–90, 690–697; 204/157.42, 204/157.62; 600/407, 437–461
See application file for complete search history.

(56) References Cited

U.S. PATENT DOCUMENTS

| | | | | |
|---|---|---|---|---|
| 6,716,172 B1 * | 4/2004 | Kerby et al. | ............... | 600/443 |
| 6,733,458 B1 * | 5/2004 | Steins et al. | ............... | 600/461 |
| 2005/0033160 A1 * | 2/2005 | Yamagata et al. | ............. | 600/425 |
| 2005/0063575 A1 * | 3/2005 | Ma et al. | ........................ | 382/128 |
| 2006/0038807 A1 | 2/2006 | Eckhardt et al. | | |
| 2008/0208046 A1 * | 8/2008 | Pierce | ............................ | 600/437 |
| 2008/0267467 A1 * | 10/2008 | Sokulin et al. | ................ | 382/128 |
| 2009/0054755 A1 * | 2/2009 | Shiibashi | ....................... | 600/407 |

FOREIGN PATENT DOCUMENTS

WO      2006/008664 A     1/2006

OTHER PUBLICATIONS

Database Compendex [online] Engineering Information, Inc., New York, NY, US; Peters Klaus-Ruediger: "Perceptually standardized imaging of digitized film for comparative ROC measurements." XP002466560.

Blume, H., et al., "Practical aspects of grayscale calibration of display systems." Proceedings of the SPIE, SPIE, Bellingham, WA, US. vol. 4323, 2001, pp. 28-41, XP002343875.

* cited by examiner

*Primary Examiner* — Amare Mengistu
*Assistant Examiner* — Vinh Lam

(57) ABSTRACT

An ultrasound imaging system includes an ultrasound probe receiving echo signals from a subject, and a processor converting echo signals received from the probe to echo data corresponding to an ultrasound image. The system also includes a grayscale mapper transforming the echo data received from the processor to a corresponding value of perception data. The grayscale mapper makes this transformation using a DICOM compliant GSDF calibration curve. The perception data is passed to a transform processor, which also receives an ambient light signal from an ambient light sensor. The transform processor converts the perception values to respective digital driving levels based on the ambient light signal and display characteristics of a display device to which the digital driving levels are applied to maintain optimal image display under varying ambient light conditions.

10 Claims, 4 Drawing Sheets

SYSTEM AND METHOD FOR DICOM COMPLIANT DISPLAY OF ULTRASOUND IMAGES IN VARYING AMBIENT LIGHT

This invention relates to medical diagnostic imaging systems and, in particular, to ultrasonic diagnostic imaging systems which ensure that a displayed image conforms to generally-accepted performance standards for displaying medical images despite changes in ambient lighting conditions.

Images of anatomical structures in the human body are commonly obtained using a wide variety of techniques. For example, images are obtained by x-ray, magnetic resonance imaging ("MRI"), and ultrasound technologies. In modern medical imaging systems, the images are captured as a digital record and stored on media or in a network storage server. The images may be viewed in real-time as they are generated, or they may be viewed using the saved digital record. In either case, the images may be viewed through a variety of displays, including, for example, cathode ray tube ("CRT") displays, plasma displays, light-emitting diode ("LED") displays, field emission displays, and organic light emitting diode displays. The appearance of the same image can differ when the image is viewed on each of these displays. Further, an image viewed on any of these displays can change as a result of operator adjustments. For example, a user may alter the brightness, contrast, or color saturation of an image. An image can also be viewed using any of these display devices in a variety of lighting conditions, which can vary with the location of the display or for other reasons, such as changes in ambient lighting conditions. As a result of these variations, there can be differences between how an image is perceived when viewed on an imaging system as the image is acquired compared to how the image is perceived when subsequently viewed on the display of a diagnostic review station.

Despite these and other variations in the manner in which medical images are displayed, it can be important for an accurate diagnosis that medical images be displayed in a consistent manner that conforms to generally accepted performance standards for displaying medical images. Efforts have been made to achieve uniform perception of the medical images between image acquisition and subsequent review. For example, the Digital Image and Communications in Medicine ("DICOM") standard attempts to ensure that medical images are perceived in a consistent manner. A part of the DICOM standard dealing with the visual presentation of images is PS 3.14. This part of the standard defines a calibration profile for medical imaging monitors, known as the Grayscale Standard Display Function ("GSDF") specification. The calibration profile provided by the GSDF specification achieves "perceptual linearization" in perceived brightness for equal differences in display input. The GSDF standard is based on the recognition that the sensitivity of the human eye to incremental changes in light level varies with the absolute intensity of light. The GSDF calibration profile therefore provides an objective, quantitative mechanism for mapping digital image values into respective luminance levels. By using a known functional relationship between digital image values and luminance levels, an image can be displayed and viewed on a different device or medium with the same diagnostic value it possesses on its original acquisition device. The GSDF standard also takes into account the level of ambient light of the viewing environments when calibrating a display device to the GSDF calibration curve. If the amount of ambient light is ignored in performing a GSDF calibration, low light levels used to display gray would be overwhelmed in an environment with elevated ambient light levels.

One variable that PS 3.14 is designed to eliminate is the variability of user preferences which a user may employ to adjust an image to what the user personally feels is a more diagnostic presentation. One environmental variable that can motivate a user to make such adjustments is the ambient lighting in the room or lab where an image is being viewed. In some instances the room may be brightly lighted to make the patient feel more comfortable and at ease, for example. In other instances the room may be more dimly lit, enabling subtle details in the displayed image to be more readily discerned by the diagnostician. In yet other instances the images may be acquired in a brightly lighted room, then transferred electronically to a workstation in a dimly lit diagnostic lab for reading by a diagnosing physician. In these variable conditions the sonographer will want to adjust the image display controls such as brightness and contrast to present an image which he or she feels is most diagnostic. This adjustment may adversely affect the image when remotely viewed, however, because the manual image adjustment may cause acoustic controls like Gain or TGC to produce poor digital images for remote viewing. Another compensation is for the sonographer to leave the display brightness/contrast unchanged, but to compensate for ambient light conditions by abnormally adjusting the acoustic imaging controls such as Gain or TGC. These adjustments could tend to adversely affect both the local viewing and the remote viewing of the digital images. Both types of adjustment can result in poor image perception or bad acoustic control settings.

Conventional monitors for displaying medical images attempt to provide GSDF calibration based on ambient light level by allowing manual adjustment of the displayed image. Adjustments are typically made using a fixed estimate or measurement of the intensity of ambient light. These estimates are based on the subjective judgment of the person making the adjustment, and they are therefore neither consistent or free from error. Further, these estimates are incorrect when the ambient light conditions differ from those extant at the time of attempted GSDF calibration, which can readily occur when the an ultrasonic imaging system is moved to a different room.

Another problem encountered with displaying ultrasound images with excessive brightness using a portable display is excessive power consumption, which manifests itself in reduced time between battery re-charges. Therefore, apart from the desirability of displaying ultrasound images in a manner that conforms to the DICOM standard, it is also desirable to avoid displaying ultrasound images with excessive brightness in order to maximize the time between battery re-charges.

There is therefore a need for an ultrasound imaging system that produces images for remote system display that consistently conform to the DICOM standard despite variations in the level of ambient light at the location of the ultrasound imaging system which acquired the images.

An ultrasound imaging system and method produces an ultrasound image for display on a review station or remote display device in a DICOM compliant manner. Echo data corresponding to the ultrasound image are first provided by suitable means. The values of the echo data are transformed to corresponding p-values using a DICOM compliant GSDF calibration curve. As a result, DICOM compliant p-values corresponding to the ultrasound image are generated. The level of ambient light in the vicinity of the display device is also sensed. The p-values are converted to respective digital driving levels based on display characteristics of the display device and the sensed level of ambient light. Thus, the sensed level of ambient light is automatically used in the conversion of the p-values to the respective digital driving levels for the ultrasound system display. The digital images may be conveyed to another display device at a remote location where they may be displayed in a perceptually linear way in compliance with the DICOM standard.

Figure 1:
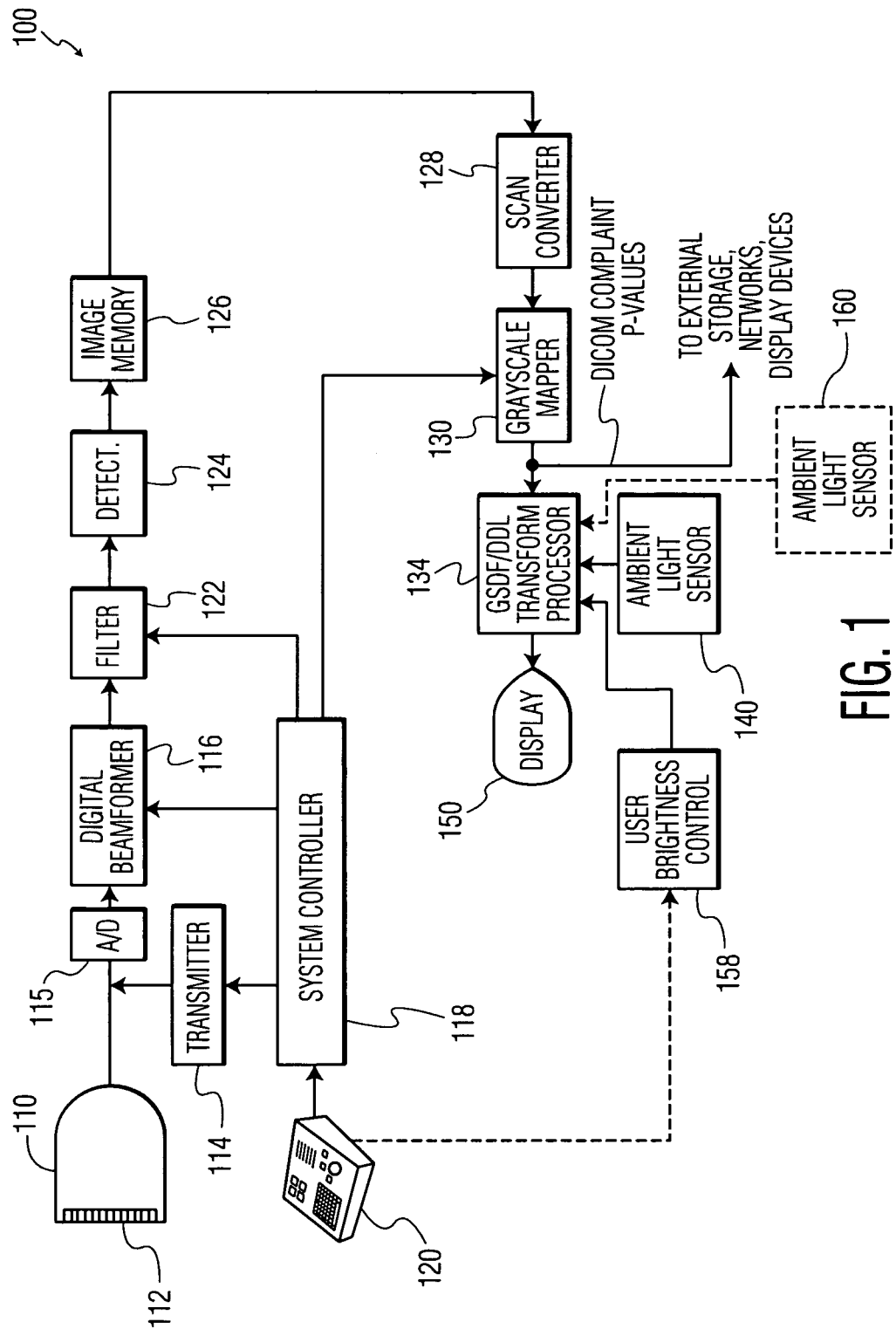
FIG. 1 is a block diagram illustrating an ultrasonic diagnostic imaging system according to one example of the present invention.

An ultrasonic diagnostic imaging system 100 according to one example of the invention is shown in FIG. 1. The imaging system 100 includes a probe or scanhead 110 having an array 112 of transducer elements. The array 112 transmits beams at different angles over an image field. The transmission of the beams is controlled by a transmitter 114, which controls the frequency, phasing and time of actuation of each of the transducer elements of the array 112 so each beam is transmitted from a predetermined origin along the array and at a predetermined angle. The echoes returned from along each beam direction are received by the elements of the array 112, digitized by an analog-to-digital ("A/D") converter 115, and coupled to a digital beamformer 116. The digital beamformer 116 delays and sums the echoes from the transducer elements of the array 112 to form a sequence of focused, coherent digital echo samples along each scanline or beam direction. The sequence of samples are used to form respective image frames corresponding to the beams formed by the beamformer 116.

The transmitter 114 and beamformer 116 are operated under control of a system controller 118, which in turn is responsive to the settings of controls on a user interface 120 operated by a user of the imaging system 100. The system controller 118 controls the transmitter 114 to transmit the desired number of scanline groups at the desired angles, transmit energies and frequencies. The system controller 118 also controls the digital beamformer 116 to properly delay and combine the received echo signals for the apertures and image depths used.

The scanline echo signals generated by the digital beamformer 116 are filtered by a programmable digital filter 122, which defines the band of frequencies of interest. When imaging harmonic contrast agents or performing tissue harmonic imaging, the passband of the filter 122 is set to pass harmonics of the transmit band. The filtered signals are then detected by a detector 124. For B mode imaging, the detector 124 performs amplitude detection of the echo signal envelope. For Doppler imaging, ensembles of echoes are assembled for each point in the image and are Doppler processed to estimate the Doppler shift or Doppler power intensity. The echo data from the scanlines of an image are collected in an image memory 126. This echo data is coupled to a scan converter 128 where the echo data is arranged in the desired image format such as a rectangular linearly scanned image or a sector-shaped image or a 3D volume rendering.

Figure 2:
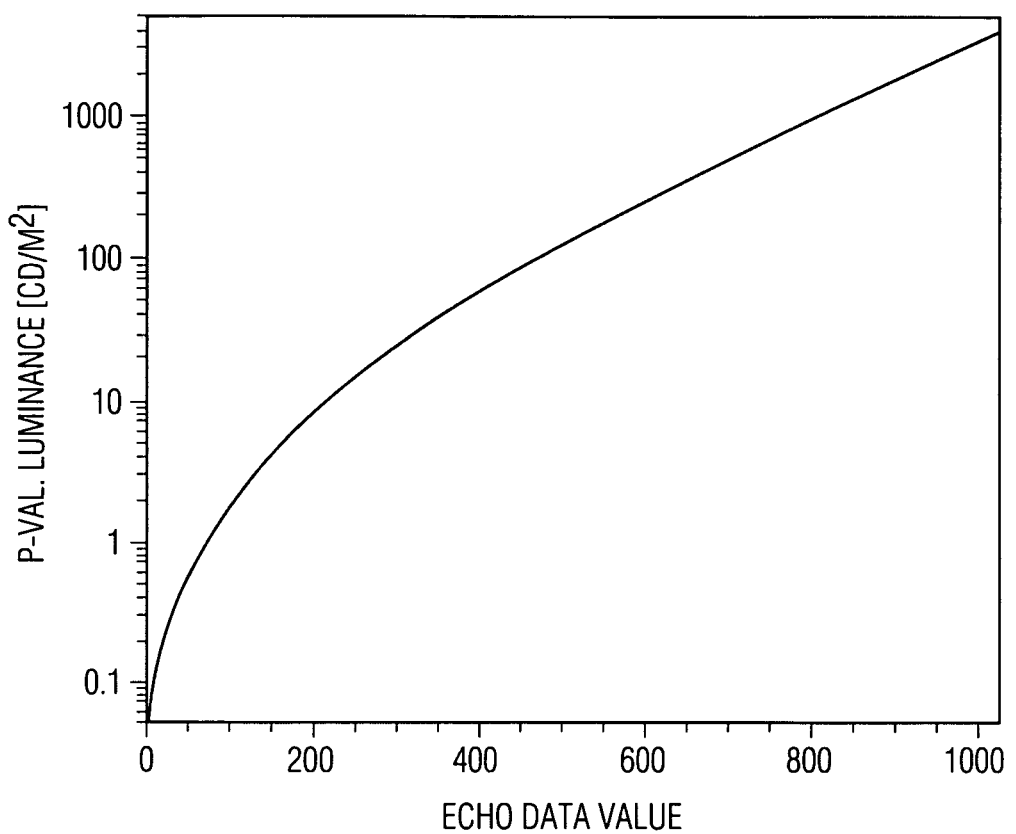
FIG. 2 is a graph illustrating a standardized grayscale display function of echo data values versus p-values, which define luminance differences that are linearly perceived by a human observer.

The echo data from the scan converter 128 are converted to a range of grayscale display values in a process known as mapping using a grayscale mapper 130. The grayscale mapper 130 transforms values corresponding to the echo data from the scan converter 128 to data corresponding to respective perception values, known as "p-values." The p-values are luminance values that linearly relate the echo data values to "just noticeable differences" in human perception in accordance with the DICOM standard in general, and the GSDF calibration curve in particular. The grayscale mapper 130 may perform this function using a lookup table, or it may do so by other means such as formulaic computation. These p-values are independent of a specific device on which an image is displayed. FIG. 2 illustrates an example of a GSDF calibration curve showing p-values corresponding to echo data values.

After the grayscale mapper 130 has mapped the image to the GSDF calibration curve, data corresponding to the image can be transferred to external networks, storage devices and display devices (not shown) such as workstations, paper printers, and film printers. When these devices are configured to respond to DICOM standard images, the images can be reproduced to the same diagnostic value they had in their original form. The images may be shown on emissive displays, such as workstation monitors or LCD displays, in a darkened room, printed on transmissive film and viewed on a radiology light-box, or printed on glossy or non-glossy photographic paper with the same diagnostic presentation in each case. The external networks, storage devices and display devices perform this function by applying the standard DICOM images to the characteristic display curve of the respective display device, which translates the standard image to the known display characteristic of the display device. The images will exhibit the same diagnostic value, within the limitations of the display device, for a variety of display devices on which they are displayed. The calibration of these softcopy review devices is performed considering the ambient light at the viewing location, which is independent of the ambient light at the image acquisition location.

Figure 3:
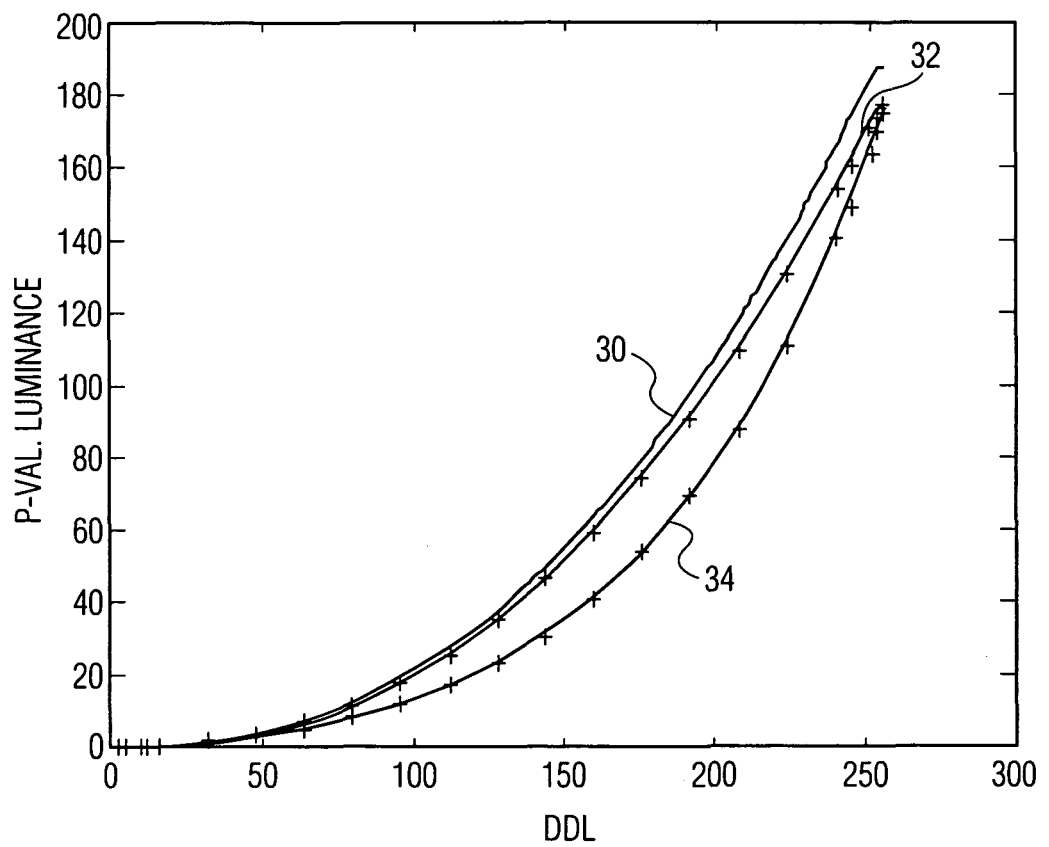
FIG. 3 is a graph illustrating the translation of p-values to digital display level ("DDL") values that are specific to a display device used in the ultrasonic diagnostic imaging system of FIG. 1.

With further reference to FIG. 1, after the echo data values have been mapped by the mapper 130 to respective p-values using the GSDF calibration curve, data corresponding to the p-values are applied to a p-value/DDL transform processor 134. The p-value/DDL transform processor 134 transforms an image mapped to DICOM calibrated p-values to a range of digital driving levels (DDLs) suitable for a particular display device 150 used in the imaging system 100. For example, the p-values applied at the input of the transform processor 134 may be mapped to a series of digital driving levels that graphically plot to a standard curve 30 for a typical CRT display device, as shown in FIG. 3. A different display device 150, however, may require a different series of DDLs. For example, the transform processor 134 may map the received p-values to a series of digital driving levels that graphically plot to a flat panel display device response curve 32. In order to faithfully reproduce the luminance levels of the standardized image on a unique display device 150, the p-values conforming to the GSDF curve must be translated according to the device-specific response curve 32. This is preferably done by a lookup table of output DDL values, which the transform processor 134 addresses using the received DICOM compliant p-values. Another display device (not shown) may have a different display response, and a translation will then be performed in order to accurately drive the different display device. When the DDL values produced by the transform processor 134 are applied to the display device 150, the display device 150 is driven by drive levels specific to the device 150, which cause the device 150 to produce images with luminance levels conforming to the human perception levels of the DICOM display standard.

The imaging system 100 also includes at least one ambient light sensor 140, which is connected to the p-value/DDL transform processor 134. The ambient light sensor 140 generates a signal indicative of the level of ambient light in the environs of the display device 150. The p-value/DDL transform processor 134 uses the signal indicative of the level of ambient light to generate a calibration curve that relates the DICOM compliant p-values from the grayscale mapper 130 to specific digital driving levels DDL for the level of ambient light corresponding to the signal from the ambient light sensor 140. As explained above, this calibration curve may be in the form of a lookup table or may be implemented by some other means. When a lookup table is used, a lookup table is generated that is specific to the characteristics of the display device 150 and the level of ambient light. The p-value/DDL transform processor 134 then uses this lookup table to transform each received p-value to a corresponding DDL value. As a result, the display device 150 will automatically present a consistent image despite variations in the level of ambient light. As the ambient light level in a room is increased or decreased or the imaging system is moved to a different room, the light sensor 140 will apply a corresponding signal to the p-value/DDL transform processor 134. The p-value/DDL transform processor 134 will then generate a new calibration curve, such as by generating a new lookup table, corresponding to the level of ambient light. The transform processor will then use this new calibration curve to convert p-values to respective DDL values.

Figure 4:
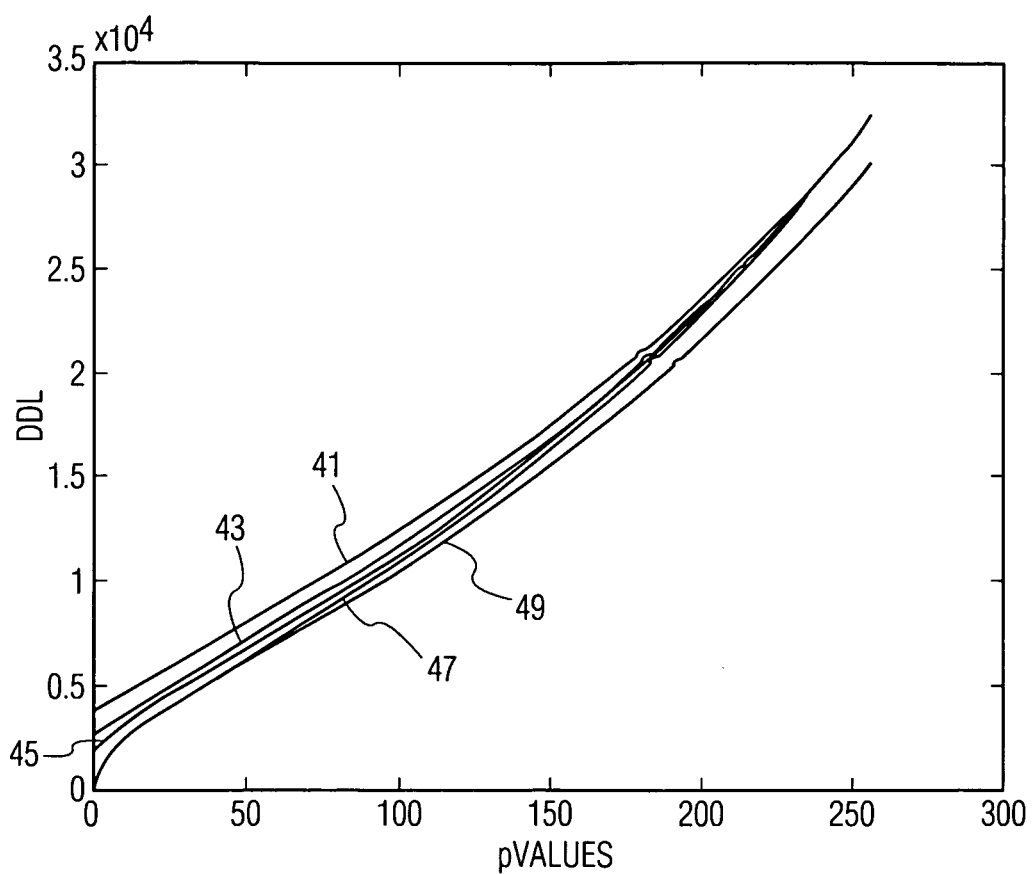
FIG. 4 is a graph showing several examples of calibration curves relating p-values to DDL values, one of which is selected in the system of FIG. 1 for respective levels of ambient light.

A set of calibration curves for different levels of ambient light is shown in FIG. 4, for example. The curve 41 for instance is relatively linear throughout its range. This curve would be used in a brightly lit room where degradation of the display dynamic range requires more compensation for low luminance levels. The higher numbered curves are used for progressively dimmer ambient room lighting levels. The curve 49 for instance applies a more rapid change between consecutive low grayscale levels, as is evident from the steeply curved shape near the origin of the graph. This display function will impose the greater differentiation in low level driving values needed to maintain the diagnostic value of the displayed image, particularly the low luminance levels, in a dimly lighted room.

Although only one ambient light sensor 140 is shown in FIG. 1, signals from a second ambient light sensor 160 may optionally be used by the p-value/DDL transform processor 134 to assist in generating a calibration curve that relates the p-values to display DDL values for the corresponding level and nature of the ambient light. For example, the ambient light sensor 140 may sense the level of ambient light falling on the screen of the display device 150 while the ambient light sensor 160 may sense the level of ambient light behind the screen. An average of the light levels sensed by both of these ambient light sensors 140, 160 could then be used to generate a new calibration curve relating received p-values to output DLL values. Alternatively, the levels of reflected light and backlight could be accounted for differently in the construct of the calibration curve.

The imaging system 100 may also include a manually adjustable brightness control 158, which allows a user to change the brightness of the image shown in the display device 150. This allows the user to make a manual adjustment based on personal judgment of the ambient light conditions. The images will still conform to the DICOM standard when the user's judgment of the ambient conditions is reasonable. The brightness adjustment can, if desired, be regarded as a change in an acoustic imaging parameter and, rather than disable GSDF, can be used to make a change to the image that appears both on the local monitor and in the exported digital image used for remote review.

Although the present invention has been described with reference to the disclosed embodiments, persons skilled in the art will recognize that changes may be made in form and detail without departing from the spirit and scope of the invention. Such modifications are well within the skill of those ordinarily skilled in the art. For example an ultrasound system can have two video outputs, one producing a signal compensated for ambient light and another producing an uncompensated video signal. The user would use the compensated video output for a display in the same viewing room as the imaging system, and the uncompensated video output for a display in a separate viewing room which may have different ambient lighting conditions. Accordingly, the invention is not limited except as by the appended claims.

We claim:

1. A method of displaying an ultrasound image on a display device, comprising:
    providing echo data corresponding to the ultrasound image;
    sensing a level of ambient light in a vicinity of the display device;
    generating DICOM (Digital Image and Communications in Medicine) compliant perception values corresponding to the ultrasound image by using a DICOM compliant GSDF (Grayscale Standard Display Function) calibration curve to transform each value of echo data to a corresponding perception value;
    converting the perception values to respective digital driving levels based on display characteristics of the display device and the sensed level of ambient light, the sensed level of ambient light being automatically used in the conversion of the perception values to the respective digital driving levels; and
    providing the digital driving levels to the display device so that the display device can display the ultrasound image.

2. The method of claim 1 wherein the act of using a DICOM compliant GSDF calibration curve to transform each value of echo data to the corresponding perception value comprises:
    generating a lookup table corresponding to the DICOM compliant GSDF calibration curve, the lookup table containing a plurality of echo data values and a plurality of perception values each of which is associated with a respective one of the echo data values; and
    using the echo data values to reference the associated perception values in the lookup table.

3. The method of claim 1 wherein the act of converting the perception values to respective digital driving levels comprises:
    generating a lookup table corresponding to the display characteristics of the display device and the sensed level of ambient light, the lookup table containing a plurality of perception values and a plurality of digital driving levels each of which is associated with a respective one of the perception values; and
    using the perception values to reference the associated digital driving levels in the lookup table.

4. The method of claim 1 wherein the act of generating a lookup table corresponding to the display characteristics of the display device and the sensed level of ambient light comprises generating a lookup table corresponding to the display characteristics of the display device, a respective lookup table corresponding to the display characteristics of the display device being generated for each sensed level of ambient light.

5. The method of claim 1 wherein the act of sensing the level of ambient light in the vicinity of the display device comprises sensing the level of ambient light in two separate locations in the vicinity of the display device.

6. The method of claim 5 wherein the act of sensing the level of ambient light in two separate locations in the vicinity of the display device comprises:
- sensing the level of ambient light on a display screen of the display device; and
- sensing the level of ambient light behind the display screen of the display device.

7. The method of claim 1, further comprising manually adjusting a brightness of the ultrasound image displayed on the display device,
- wherein adjusting the brightness is regarded as a change in an acoustic imaging parameter which makes a change to the ultrasound image that appears both on a local display device and in an image signal used for remote review.

8. The method of claim 1 wherein the display device comprises a flat panel display device.

9. The method of claim 1 wherein the display device comprises a cathode ray tube display device.

10. The method of claim 1 wherein the act of using a DICOM compliant GSDF calibration curve to transform each value of echo data to a corresponding perception value comprises mapping each value of echo data to a corresponding grayscale perception value.

\* \* \* \* \*